US006355862B1

(12) United States Patent
Handa et al.

(10) Patent No.: US 6,355,862 B1
(45) Date of Patent: Mar. 12, 2002

(54) FRUIT QUALITY BY INHIBITING PRODUCTION OF LIPOXYGENASE IN FRUITS

(75) Inventors: Avtar K. Handa, West Lafayette, IN (US); Kurt D. Kausch, Chicago, IL (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 09/051,465

(22) PCT Filed: Oct. 11, 1996

(86) PCT No.: PCT/US96/16387

§ 371 Date: Jul. 31, 1998

§ 102(e) Date: Jul. 31, 1998

(87) PCT Pub. No.: WO97/13851

PCT Pub. Date: Apr. 17, 1997

Related U.S. Application Data

(60) Provisional application No. 60/005,404, filed on Oct. 13, 1995.

(51) Int. Cl.[7] ........................ C12N 15/29; C12N 15/82; C12N 15/54; A01H 5/00
(52) U.S. Cl. ........................ 800/290; 800/278; 800/283; 800/284; 800/286; 800/317.4; 435/411; 435/419; 435/320.1; 435/468; 435/193; 536/23.6
(58) Field of Search ................................ 800/278, 286, 800/284, 290, 283, 317.4; 435/320.1, 419, 411, 468, 193; 536/23.6

(56) References Cited

U.S. PATENT DOCUMENTS

| | | | |
|---|---|---|---|
| 5,107,065 A | 4/1992 | Shewmaker et al. | 800/205 |
| 5,254,800 A | 10/1993 | Bird et al. | 800/205 |
| 5,296,376 A | 3/1994 | Bridges et al. | 435/320.1 |
| 5,413,937 A | 5/1995 | Bridges et al. | 435/320.1 |
| 5,453,566 A | 9/1995 | Shewmaker et al. | 800/205 |
| 5,844,121 A | * 12/1998 | Keller | 800/205 |

OTHER PUBLICATIONS

Ohgawara et al. Protoplasma 116: 145–148, 1983.*
Smith et al. Nature 334: 724–729, Aug. 1988.*
Ferrie, Bonita J., Beaudoin, Nathalie, Burkhart, William, Bowsher, Caroline G., and Rothstein, Steven J., "The Cloning of Two Tomato Lipoxygenase Genes and Their Differential Expression during Fruit Ripening." Plant Physiol. 106:109–118 (1994).
Kausch, Kurt D. and Handa, Avtar K., "Molecular Cloning and Nucleotide Sequence of a Lipoxygenase cDNA from Ripening Tomato Fruit." Plant Physiol. 107:669–670 (1995).

* cited by examiner

*Primary Examiner*—David T. Fox
(74) *Attorney, Agent, or Firm*—Woodard, Emhardt, Naughton, Moriarty & McNett

(57) ABSTRACT

The present invention relates generally to a transgenic fruit-bearing plant having a foreign nucleotide sequence inserted into its genome which is substantially similar to a portion of the plant's fruit ripening specific lipoxygenase cDNA. Transgenic plants according to the present invention produce fruits having modified and surprisingly superior ripening characteristics, including improved quality and texture, greater firmness, longer shelf life, better packaging and storage characteristics, and improved processing characteristics. Also provided are transgenic fruits; transgenic plant cells; methods for making transgenic plants, fruits and plant cells; methods for inhibiting lipoxygenase production in plants; isolated nulceic acid sequences; and vectors comprising these isolated nucleotide sequences.

14 Claims, 8 Drawing Sheets

FIG. 1
SEQ ID NO:1

```
 158            TTC AGTTGTTGAT GGCATTTCTG ATTTACTTGG CCAAAAAGTC
 201 TCTATCCAAT TGATAAGTGG TTCTGTTAAT TATGATGGTT TGGAAGGGAA
 251 ACTGAGCAAT CCAGCATACT TAGAGAGTTG GCTTACAGAC ATCACCCCAA
 301 TAACAGCAGG GGAATCAACT TTTAGTGTTA CATTTGACTG GGATCGTGAC
 351 GAGTTTGGAG TTCCAGGAGC ATTCATCATC AAGAATCTTC ATCTTAATGA
 401 GTTCTTTCTC AAGTCACTCA CACTCGAAGA TGTTCCTAAT TATGGAAAAA
 451 TCCATTTTGT ATGCAATTCT TGGGTTTATC CTGCTTTTAG ATACAAGTCT
 501 GACCGCATTT TCTTTGCCAA TCAGGCTTAT CTCCCAAGTG AAACACCACA
 551 ACCATTGCGA AAATACAGAG AAAATGAACT GGTAGCTTTG CGAGGAGATG
 601 GAACTGGAAA GCTTGAAGAA TGGACAGGG TTTATGATTA TGCTTGCTAC
 651 AATGACTTGG GTGAACCAGA TAAGGGGGAA GAGTATGCTA GGCCTATCCT
 701 TGGAGGGTCC TCTGAGTACC CGTATCCTCG TAGAGGCAGG ACAGGCCGCG
 751 AACCAACCAA AGCAGATCCT AATTGCGAGA GCAGGAACCC ATTGCCTATG
 801 AGCTTAGACA TATATGTCCC AAGGGACGAG CGATTTGGTC ATGTGAAGAA
 851 GTCAGACTTT TTGACGTCGT CCTTAAAATC CTCTTTGCAA ACGCTTCTCC
 901 CTGCGTTTAA GGCTTTGTGC GATAACACGC CTAATGAGTT CAATAGCTTT
 951 GCGGATGTAC TTAATCTCTA TGAAGGAGGA ATCAAGTTGC CTGAAGGCCC
1001 TTGGTTGAAA GCCATTACTG ATAACATTTC CTCAGAGATA CTAAAGACA
1051 TCCTTCAAAC GGATGGTCAA GGCCTACTTA AGTACCCAAC TCCTCAGGTT
1101 ATTCAAGGCG ATAAAACTGC ATGGAGGACG GATGAAGAAT TTGGGAGAGA
1151 AATGTTGGCA GGATCCAATC CTGTCTTAAT CAGTAGACTC CAAGAATTTC
1201 CTCCGAAGAG CAAGTTGGAT CCAACCATAT ATGGAAACCA AACAGTACA
1251 ATTACCACAG AACATGTACA GGATAAGTTG AATGGATTAA CAGTGAATGA
1301 GGCAATCAAG AGTAACAGGT TATTCATATT GAACCACCAT GACATCGTGA
1351 TGCCACTATT GAGGAAAATT AACATGTCAG CAAACACAAA AGCCTATGCC
1401 TCAAGAACTC TGCTCTTCCT ACAAGATGAT AGAACTTTGA AGCCACTAGC
1451 AATTGAACTA AGCTTGCCAC ATCCAGACGG AGATCAATTT GGTACTGTTA
1501 GTAAAGTATA TACACCAGCT GACCAAGGTG TTGAAGGTTC TATCTGGCAG
1551 TTTGCCAAAG CCTATGTAGC AGTGAATGAC ATGGGCATTC ATCAGCTCAT
1601 TAGCCACTGG TTGAATACAC ACGCGGTGAT CGAACCATTT GTGATTGCAA
1651 CAAATAGGCA TCTAAGTGTG CTTCATCCCA TTCATAAACT TCTTCATCCT
1701 CATTTCCGTA ACACGATGAA CATAAATGCT TTAGCAAGAG AGACCTTGAC
1751 CTATGATGGT GGTTTTGAGA CGTCTCTTTT TCCTGCCAAA TATTCCATGG
1801 AAATGTCAGC AGCAGCTTAC AAAGATTGGG TTTTCCCTGA CAAGCACTT
1851 CCTGCTGATC TCCTCAAAAG AGGAGTGGCT GTTGAGGACT TGAGCTCCCC
1901 ACATGGCATT CGTTTACTGA TTCTGGACTA TCCATATGCT GTTGATGGCT
1951 TGGAAATTTG GGCAGCAATC AAAAGTTGGG TAACAGAATA TTGCAAGTTC
2001 TATTACAAAT CTGACGAGAC AGTAGAGAAA GACACTGAAC TCCAAGCTTG
2051 GTGGAAGGAG CTCCGCGAAG AAGGACATGG CGACAAGAAA GATGAGGCTT
2101 GGTGGCCTAA ACTGCAAACT CGACAAGAGC TCAGAGATTG TTGCACCATC
2151 ATTATATGGA TAGCTTCAGC ACTTCATGCA GCACTCCATT TTGGCTTATA
2201 CTCTTACGCT GGTTATCTCC CTAATCGCCC TACTTTAAGC TGTAATTTGA
2251 TGCCAGAGCC AGGAAGTGTT GAGTATGAAG AGCTCAAGAC AAATCCAGAC
2301 AAGGTATTCC TAAAAACATT TGTTCCTCAG TTGCAATCAC TGCTTGAAAT
2351 TTCCATCTTT GAGGTCTCGT CAAGGCATGC TTCAGATGAG GTTTACTTGG
2401 GACAAAGGGA CTCAATTGAA TGGACAAAGG ATAAAGAACC ACTTGTAGCT
2451 TTTGAGAGGT TTGGAAAGAT GCTAAGTGAT ATCGAGAATC GAATTATGAT
2501 AATGAATAGT CATAAGAGTT GGAAGAACAG GTCAGGGCCT GTTAACGTTC
2551 CATATACGTT GCTCTTTCCC ACAAGTGAAG AGGGACTCAC AGGCAAAG
```

FIG. 2

SEQ ID NO:2

```
   1  TTTTCTTAAT TAAAAAAAAA ATATTTCTGT TTAAATAGTT AATCATGTCT
  51  TTGGGTGGAA TTGTGGATGC CATCCTTGGA AAAGATGATA GGCCAAAAGT
 101  GAAAGGAAGA GTGATTTTGA TGAAAAAAAA TGTTCTAGAC TTCATTAATA
 151  TAGGTGCTTC AGTTGTTGAT GGCATTTCTG ATTTACTTGG CCAAAAAGTC
 201  TCTATCCAAT TGATAAGTGG TTCTGTTAAT TATGATGGTT TGGAAGGGAA
 251  ACTGAGCAAT CCAGCATACT TAGAGAGTTG GCTTACAGAC ATCACCCCAA
 301  TAACAGCAGG GGAATCAACT TTTAGTGTTA CATTTGACTG GGATCGTGAC
 351  GAGTTTGGAG TTCCAGGAGC ATTCATCATC AAGAATCTTC ATCTTAATGA
 401  GTTCTTTCTC AAGTCACTCA CACTCGAAGA TGTTCCTAAT TATGGAAAAA
 451  TCCATTTTGT ATGCAATTCT TGGGTTTATC CTGCTTTTAG ATACAAGTCT
 501  GACCGCATTT TCTTTGCCAA TCAGGCTTAT CTCCCAAGTG AAACACCACA
 551  ACCATTGCGA AAATACAGAG AAAATGAACT GGTAGCTTTG CGAGGAGATG
 601  GAACTGGAAA GCTTGAAGAA TGGGACAGGG TTTATGATTA TGCTTGCTAC
 651  AATGACTTGG GTGAACCAGA TAAGGGGGAA GAGTATGCTA GGCCTATCCT
 701  TGGAGGGTCC TCTGAGTACC CGTATCCTCG TAGAGGCAGG ACAGGCCGCG
 751  AACCAACCAA AGCAGATCCT AATTGCGAGA GCAGGAACCC ATTGCCTATG
 801  AGCTTAGACA TATATGTCCC AAGGGACGAG CGATTTGGTC ATGTGAAGAA
 851  GTCAGACTTT TTGACGTCGT CCTTAAAATC CTCTTTGCAA ACGCTTCTCC
 901  CTGCGTTTAA GGCTTTGTGC GATAACACGC CTAATGAGTT CAATAGCTTT
 951  GCGGATGTAC TTAATCTCTA TGAAGGAGGA ATCAAGTTGC CTGAAGGCCC
1001  TTGGTTGAAA GCCATTACTG ATAACATTTC CTCAGAGATA CTAAAGACA
1051  TCCTTCAAAC GGATGGTCAA GGCCTACTTA AGTACCCAAC TCCTCAGGTT
1101  ATTCAAGGCG ATAAAACTGC ATGGAGGACG GATGAAGAAT TGGGAGAGA
1151  AATGTTGGCA GGATCCAATC CTGTCTTAAT CAGTAGACTC CAAGAATTTC
1201  CTCCGAAGAG CAAGTTGGAT CCAACCATAT ATGGAAACCA AAACAGTACA
1251  ATTACCACAG AACATGTACA GGATAAGTTG AATGGATTAA CAGTGAATGA
1301  GGCAATCAAG AGTAACAGGT TATTCATATT GAACCACCAT GACATCGTGA
1351  TGCCACTATT GAGGAAAATT AACATGTCAG CAAACACAAA AGCCTATGCC
1401  TCAAGAACTC TGCTCTTCCT ACAAGATGAT AGAACTTTGA AGCCACTAGC
1451  AATTGAACTA AGCTTGCCAC ATCCAGACGG AGATCAATTT GGTACTGTTA
1501  GTAAAGTATA TACACCAGCT GACCAAGGTG TTGAAGGTTC TATCTGGCAG
1551  TTTGCCAAAG CCTATGTAGC AGTGAATGAC ATGGGCATTC ATCAGCTCAT
1601  TAGCCACTGG TTGAATACAC ACGCGGTGAT CGAACCATTT GTGATTGCAA
1651  CAAATAGGCA TCTAAGTGTG CTTCATCCCA TTCATAAACT TCTTCATCCT
1701  CATTTCCGTA ACACGATGAA CATAAATGCT TTAGCAAGAG AGACCTTGAC
1751  CTATGATGGT GGTTTTGAGA CGTCTCTTTT TCCTGCCAAA TATTCCATGG
1801  AAATGTCAGC AGCAGCTTAC AAAGATTGGG TTTTCCCTGA ACAAGCACTT
1851  CCTGCTGATC TCCTCAAAAG AGGAGTGGCT GTTGAGGACT TGAGCTCCCC
1901  ACATGGCATT CGTTTACTGA TTCTGGACTA TCCATATGCT GTTGATGGCT
1951  TGGAAATTTG GGCAGCAATC AAAAGTTGGG TAACAGAATA TTGCAAGTTC
```

*FIG. 2 (cont.)*

```
2001 TATTACAAAT CTGACGAGAC AGTAGAGAAA GACACTGAAC TCCAAGCTTG
2051 GTGGAAGGAG CTCCGCGAAG AAGGACATGG CGACAAGAAA GATGAGGCTT
2101 GGTGGCCTAA ACTGCAAACT CGACAAGAGC TCAGAGATTG TTGCACCATC
2151 ATTATATGGA TAGCTTCAGC ACTTCATGCA GCACTCCATT TTGGCTTATA
2201 CTCTTACGCT GGTTATCTCC CTAATCGCCC TACTTTAAGC TGTAATTTGA
2251 TGCCAGAGCC AGGAAGTGTT GAGTATGAAG AGCTCAAGAC AAATCCAGAC
2301 AAGGTATTCC TAAAAACATT TGTTCCTCAG TTGCAATCAC TGCTTGAAAT
2351 TTCCATCTTT GAGGTCTCGT CAAGGCATGC TTCAGATGAG GTTTACTTGG
2401 GACAAAGGGA CTCAATTGAA TGGACAAAGG ATAAAGAACC ACTTGTAGCT
2451 TTTGAGAGGT TTGGAAAGAT GCTAAGTGAT ATCGAGAATC GAATTATGAT
2501 AATGAATAGT CATAAGAGTT GGAAGAACAG GTCAGGGCCT GTTAACGTTC
2551 CATATACGTT GCTCTTTCCC ACAAGTGAAG AGGGACTCAC AGGCAAAGGA
2601 ATTCCCAACA GTGTGTCTAT ATAGAACTTA TTATTCAATC AGTTTGTTGT
2651 GCTTGTGTTA CTTGTTATTC CCAACCAAAT AAACTCTTTG TTCCAAATAA
2701 AGAGTATTGT ATTGTATTGT CTTGTGTGTT GTGTTGTATT GTATTATATT
2751 GTATAGTATT ATTGATTTAA ATACAATGTT TGTTGCACTT GTTTCTTGTT
2801 ATTCCCAACC AAATAAACTC TTTGTTCCAA ATAAAGCTGT AGTTGGTTTT
2851 AAAAAAAAAA AAAAAAAAA A
```

FIG. 3

SEQ ID NO:3

```
  1  TTTTCTTAAT TAAAAAAAAA ATATTTCTGT TTAAATAGTT AATCATGTCT
 51  TTGGGTGGAA TTGTGGATGC CATCCTTGGA AAAGATGATA GGCCAAAAGT
101  GAAAGGAAGA GTGATTTTGA TGAAAAAAAA TGTTCTAGAC TTCATTAATA
151  TAGGTGCTTC AGTTGTTGAT GGCATTTCTG ATTTACTTGG CCAAAAAGTC
201  TCTATCCAAT TGATAAGTGG TTCTGTTAAT TATGATGGTT TGGAAGGGAA
251  ACTGAGCAAT CCAGCATACT TAGAGAGTTG GCTTACAGAC ATCACCC
```

*Fig. 4*

Nucleotide sequence of ripening-specific LOX
cDNA used for chimeric gene constructions.

SEQ ID NO:4

```
   1   TTTTCTTAAT TAAAAAAAAA ATATTTCTGT TTAAATAGTT AATCATGTCT
  51   TTGGGTGGAA TTGTGGATGC CATCCTTGGA AAAGATGATA GGCCAAAAGT
 101   GAAAGGAAGA GTGATTTTGA TGAAAAAAAA TGTTCTAGAC TTCATTAATA
 151   TAGGTGCTTC AGTTGTTGAT GGCATTTCTG ATTTACTTGG CCAAAAAGTC
 201   TCTATCCAAT TGATAAGTGG TTCTGTTAAT TATGATGGTT TGGAAGGGAA
 251   ACTGAGCAAT CCAGCATACT TAGAGAGTTG GCTTACAGAC ATCACCCCAA
 301   TAACAGCAGG GGAATCAACT TTTAGTGTTA CATTTGACTG GGATCGTGAC
 351   GAGTTTGGAG TTCCAGGAGC ATTCATCATC AAGAATCTTC ATCTTAATGA
 401   GTTCTTTCTC AAGTCACTCA CACTCGAAGA TGTTCCTAAT TATGGAAAAA
 451   TCCATTTTGT ATGCAATTCT TGGGTTTATC CTGCTTTTAG ATACAAGTCT
 501   GACCGCATTT TCTTTGCCAA TCAGGCTTAT CTCCCAAGTG AAACACCACA
 551   ACCATTGCGA AAATACAGAG AAAATGAACT GGTAGCTTTG CGAGGAGATG
 601   GAACTGGAAA GCTTGAAGAA TGGGACAGGG TTTATGATTA TGCTTGCTAC
 651   AATGACTTGG GTGAACCAGA TAAGGGGGAA GAGTATGCTA GGCCTATCCT
 701   TGGAGGGTCC TCTGAGTACC CGTATCCTCG TAGAGGCAGG ACAGGCCGCG
 751   AACCAACCAA AGCAGATCCT AATTGCGAGA GCAGGAACCC ATTGCCTATG
 801   AGCTTAGACA TATATGTCCC AAGGGACGAG CGATTGGTC ATGTGAAGAA
 851   GTCAGACTTT TTGACGTCGT CCTTAAAATC CTCTTTGCAA ACGCTTCTCC
 901   CTGCGTTTAA GGCTTTGTGC GATAACACGC TAATGAGTT CAATAGCTTT
 951   GCGGATGTAC TTAATCTCTA TGAAGGAGGA ATCAAGTTGC CTGAAGGCCC
1001   TTGGTTGAAA GCCATTACTG ATAACATTTC CTCAGAGATA CTAAAAGACA
1051   TCCTTCAAAC GGATGGTCAA GGCCTACTTA AGTACCCAAC TCCTCAGGTT
1101   ATTCAAGGCG ATAAAACTGC ATGGAGGACG GATGAAGAAT TTGGGAGAGA
1151   AATGTTGGCA GGATCCAATC CTGTCTTAAT CAGTAGACTC CAAGAATTTC
1201   CTCCGAAGAG CAAGTTGGAT CCAACCATAT ATGGAAACCA AAACAGTACA
1251   ATTACCACAG AACATGTACA GGATAAGTTG AATGGATTAA CAGTGAATGA
1301   GGCAATCAAG AGTAACAGGT TATTCATATT GAACCACCAT GACATCGTGA
1351   TGCCACTATT GAGGAAAATT AACATGTCAG CAAACACAAA AGCCTATGCC
1401   TCAAGAACTC TGCTCTTCCT ACAAGATGAT AGAACTTTGA AGCCACTAGC
1451   AATTGAACTA AGCTTGCCAC ATCCAGACGG AGATCAATTT GGTACTGTTA
1501   GTAAAGTATA TACACCAGCT GACCAAGGTG TTGAAGGTTC TATCTGGCAG
1551   TTTGCCAAAG CCTATGTAGC AGTGAATGAC ATGGGCATTC ATCAGCTCAT
1601   TAGCCACTGG TTGAATACAC ACGCGGTGAT CGAACCATTT GTGATTGCAA
1651   CAAATAGGCA TCTAAGTGTG CTTCATCCCA TTCATAAACT TCTTCATCCT
1701   CATTTCCGTA ACACGATGAA CATAAATGCT TTAGCAAGAG AGACCTTGAC
1751   CTATGATGGT GGTTTTGAGA CGTCTCTTTT TCCTGCCAAA TATTCCATGG
1801   AAATGTCAGC AGCAGCTTAC AAAGATTGGG TTTTCCCTGA ACAAGCACTT
```

*Fig. 4 (cont.)*

```
1851 CCTGCTGATC TCCTCAAAAG AGGAGTGGCT GTTGAGGACT TGAGCTCCCC
1901 ACATGGCATT CGTTTACTGA TTCTGGACTA TCCATATGCT GTTGATGGCT
1951 TGGAAATTTG GGCAGCAATC AAAAGTTGGG TAACAGAATA TTGCAAGTTC
2001 TATTACAAAT CTGACGAGAC AGTAGAGAAA GACACTGAAC TCCAAGCTTG
2051 GTGGAAGGAG CTCCGCGAAG AAGGACATGG CGACAAGAAA GATGAGGCTT
2101 GGTGGCCTAA ACTGCAAACT CGACAAGAGC TCAGAGATTG TTGCACCATC
2151 ATTATATGGA TAGCTTCAGC ACTTCATGCA GCACTCCATT TTGGCTTATA
2201 CTCTTACGCT GGTTATCTCC CTAATCGCCC TACTTTAAGC TGTAATTTGA
2251 TGCCAGAGCC AGGAAGTGTT GAGTATGAAG AGCTCAAGAC AAATCCAGAC
2301 AAGGTATTCC TAAAAACATT TGTTCCTCAG TTGCAATCAC TGCTTGAAAT
2351 TTCCATCTTT GAGGTCTCGT CAAGGCATGC TTCAGATGAG GTTTACTTGG
2401 GACAAAGGGA CTCAATTGAA TGGACAAAGG ATAAAGAACC ACTTGTAGCT
2451 TTTGAGAGGT TTGGAAAGAT GCTAAGTGAT ATCGAGAATC GAATTATGAT
2501 AATGAATAGT CATAAGAGTT GGAAGAACAG GTCAGGGCCT GTTAACGTTC
2551 CATATACGTT GCTCTTTCCC ACAAGTGAAG AGGGACTCAC AGGCAAAGGA
2601 ATTCCCAACA GTGTGTCTAT ATAGAACTTA TTATTCAATC AGTTTGTTGT
2651 GCTTGTGTTA CTTGTTATTC CCAACCAAAT AAACTCTTTG TTCCAAATAA
2701 AGAGTATTGT ATTGTATTGT CTTGTGTGTT GTGTTGTATT GTATTATATT
2751 GTATAGTATT ATTGATTTAA ATACAATGTT TGTTGCACTT GTTTCTTGTT
2801 ATTCCCAACC AAATAAACTC TTTGTTCCAA ATAAAGCTGT AGTTGGTTTT
2851 AAAAAAAAAA AAAAAAAAA A
```

US 6,355,862 B1

FRUIT QUALITY BY INHIBITING PRODUCTION OF LIPOXYGENASE IN FRUITS

This application is a 371 of PCT/US96/16387 filed Oct. 11, 1996, which claims priority to provisional application Number 60/005,404 filed Oct. 13, 1995.

BACKGROUND OF THE INVENTION

1. Field of the Invention

The present invention relates to isolated nucleotide sequences; methods for using the sequences to make transgenic plants which produce edible fruits having improved firmness and longevity; and vectors having the nucleotide sequences incorporated therein. More specifically, the present invention relates to transgenic plants and methods for making the same, the genomes of said plants having incorporated therein foreign nucleotide sequences which function to inhibit production of fruit ripening specific lipoxygenase ("FRS-LOX") in a ripening fruit. The inhibition of FRS-LOX gene expression provides a mechanism to improve characteristics of a fruit, including controlling fruit senescence and tissue softening associated with post-maturation Processes.

2. Discussion of Related Art

Biochemistry of Lipoxygenases

Lipoxygenases ("LOXs") are nonheme iron-containing dioxygenases that catalyze the incorporation of molecular oxygen into unsaturated fatty acids containing cis, cis 1,4-pentadiene structure to yield a 1-hydroperoxy-2-4-trans, cis pentadiene product. Typical substrates for LOXs in plants are linoleate (C18:2) and linolenate (C18:3) fatty acids, while animal LOXs prefer arachidonate (C20:4). Some LOXs are able to act on substituted fatty acid substrates, while others require free fatty acids. LOXs can vary in respect to (1) the site of primary hydrogen abstraction, (2) the direction of the double bond shifts in the primary radicle leading to the hydroperoxide product and (3) the stereospecificity of both hydrogen abstraction and dioxygen insertion (Ford-Hutchinson et al., Annu. Rev. Biochem. 63:383, 1994).

In plants, most fatty acids are esterified to a glycerol backbone in the form of glycerolipids and lipases are thought to cleave these phosopholipids into usable plant LOX substrates (free fatty acids). The LOX-catalyzed fatty acid hydroperoxides serve as intermediates for a number of secondary reactions leading to jasmonic acid, traumatin, traumatic acid, volatile alcohols (hexanal), aldehydes, ketols and 9C oxo fatty acids (Vick and Zimmerman, Biochemistry of Plants, Vol. 9:53, 1987; Hildebrand, Physiol. Plantarum 76:249, 1989). The 5-LOX from humans is representative of a unique type of LOX that requires the association of the 5-LOX Activating Protein (FLAP) for activity. Also, a LOX from the rabbit reticulocyte has been reported to attack mitochondrial membranes in the absence of any lipid hydrolyzing enzymes during the maturation of erythroid cells (Schewe et al., Adv. Enzymol. 58:191, 1986).

Lipoxygenases: A Multigenic Family

LOXs have been found in a wide range of organisms including higher plants, animals, yeast, fungi and cyanobacterium (Siedow, Annu. Rev. Plant Physiol. Plant Mol. Biol. 42:145, 1991). LOX multigenic families have been characterized in several plant and animal species (Siedow, Annu. Rev. Plant Physiol. Plant Mol. Biol. 42:145, 1991; Ford-Hutchinson et al., Annu. Rev. Biochem. 63:383, 1994). The best characterized plant LOXs are the three soybean cotyledon LOX monomer isozymes; L-1, L-2 and L-3, all globular, water soluble proteins with MWs of about 96 kD. LOXs from rice, soybean, cotton, sunflower, tomato, Arabidopsis, cucumber, kiwi and tobacco are some that have been identified and are on the order of 95 kD, with the exception of pea (72–108 kD). Sequences reported for plant LOXs are approximately 60% homologous to one another. Human LOXs are about 60% homologous and are only 25% identical to plant LOXs (Ford-Hutchinson et al., Annu. Rev. Biochem. 63:383, 1994). Some of the plant LOXs are larger than animal LOXs and show homology with them only in limited regions (Minor et al., Biochem. 32:6320, 1993).

Biological Role(s) of Lipoxygenases

The function of various LOX isozymes in plant and mammalian systems is unknown. The hydroperoxide products from some animal LOXs serve as precursors in the production of leukotrienes and lipoxins, regulatory molecules involved in responses include leukotiene induced altered cell functions such as chemotaxis and chemokinesis. Roles of LOX during all stages of plant growth and development have been speculated (Siedow, Annu. Rev. Plant Physiol. Plant Mol. Bio. 42:145, 1991). LOX activity has been demonstrated in rapidly growing young tissues (germinating seedlings). It has been suggested that jasmonic acid and hydroperoxide free radicles, primary and secondary products of LOX, may play roles in plant senescence by promoting cell membrane deterioration, inhibiting protein synthesis and chloroplast photochemical activity. Upon tissue wounding, increases in LOX activity and mRNA accumulation have been seen in some plants. Traumatin and traumatic acid may be involved in wound healing of damaged plant tissues (Hildebrand, Physio. Plantarum 76:249, 1989). Another secondary LOX product, hexanal, may be produced in response to pest/pathogen attack. However, no evidence to support any of these hypotheses has been obtained.

Shelf Life of Fruits and Vegetables

Fruits and vegetables are highly perishable crops and significant losses often occur after their harvest but before they reach the consumer. The primary causes of these losses are the inability to control: 1) senescence of these crops; 2) the ripening process in fruits; and 3) ripening-and sensescence-associated tissue softening. One of the objectives of plant breeders for many years has been to control these processes by introducing traits from wild germ plasm into the cultivated species. In recent years, attempts have been made to use recombinant DNA technology to modify some of these traits. Both antisense and co-suppression technologies have been used in some crop plants to modify the expression of specific genes which may have deleterious effects on plant growth and development or crop productivity in general. However, none have proven fully satisfactory in reducing the rate of tissue softening associated with post-maturation plant processes.

Major transitions in fruit development and metabolism accompany the initiation of fruit ripening. In addition to alterations in pigment biosynthesis and production of volatile compounds, fruits undergo significant changes in texture during ripening. The biochemical bases for ripening- and senescence-associated fruit softening are not yet understood; however, dissolution of the middle lamella and cell wall separation due to depolymerization of pectins by polygalacturonase as well as loss of calcium have been suggested to contribute to fruit softening. Only slight improvement in fruit integrity has been reported in fruits with low polygalacturonase activity (Schuch et al. HortScience 26: 1517, 1991; Carrington et al., Plant Physiology 103: 429, 1993).

There is a need for transgenic plants which produce fruits having modified ripening and post-maturation characteristics including improved quality and texture, greater firmness, longer shelf life, better packing and storage characteristics and improved processing characteristics.

SUMMARY OF THE INVENTION

The invention described herein features inhibiting the expression of fruit ripening specific lipoxygenase ("FRS-LOX") in a plant, specifically in cells of a fruit of the plant. For instance, foreign DNA can be introduced into cells to reduce FRS-LOX production. In a preferred embodiment, the cell is a plant cell and the genetic material is a sense or antisense fragment substantially similar to a portion of the FRS-LOX cDNA shown in SEQ ID NO:4. Most preferably, the cell is a cell of a fruit-bearing plant, such as a tomato plant cell.

It is expected that the present invention can be applied to the inhibition of FRS-LOX gene products in a wide variety of useful plants. These may include, for example, commercially important fruit-bearing plants in which post-maturation weakening reduces economic value, such as melons, peaches, bananas, apples, strawberries, kiwi fruit, and in particular the tomato.

The present inventors have made the surprising discoveries that (1) inhibition of FRS-LOX greatly improves fruit qualities such as, for example, firmness and shelf life; and (2) antisense and co-suppression (sense) technologies can be successfully used to inhibit FRS-LOX gene expression in plants so as to provide fruits having superior qualities such as, for example, firmness and shelf life. It is believed that improved fruit qualities result from reduced activity of degradative pathways (e.g., membrane deterioration); however, it is not intended that the present invention be limited to this theory.

Briefly describing one aspect of the present invention, there is provided a method for making a transformed plant having improved fruit quality comprising inserting a nucleotide sequence into DNA of the plant in a sense or antisense orientation under a suitable promoter so as to inhibit production of lipoxygenase in the fruit of the plant as it ripens. In a preferred method, a sequence of nucleotides is inserted into a target cell by providing a vector comprising the nucleotide sequence and contacting the vector with the target cell.

Additional aspects of the present invention include vectors having incorporated therein nucleotide sequences having substantial similarity to all or a portion of the sequence of SEQ ID NO:4(FIG. 4).

Additional aspects of the invention include constructs selected from the group consisting of pMLSL, PMLAL, pUSL2, pUAL2, pUEL300S and pUEL300A, which are useful for inserting foreign DNA into a plant cell genome.

According to other aspects of the present invention there are provided transgenic fruits, transgenic plants and transgenic host cells, preferably plant cells such as germ cells and cotyledon cells. These various transgenic hosts are preferably transformed by having incorporated into their genomes, nucleotide sequences as delineated above and described in greater detail below.

It is an object of the present invention to provide transgenic plants which produce fruits having modified ripening characteristics, including improved quality and texture, greater firmness, longer shelf life, better packaging and storage characteristics and improved processing characteristics.

Further objects, advantages, and features of the present invention will be apparent from the detailed description which follows.

BRIEF DESCRIPTION OF THE DRAWINGS

FIG. 1 sets forth the nucleotide sequence of one portion of the fruit ripening specific lipoxygenase ("FRS-LOX") gene which is inserted into a plant cell genome according to one preferred embodiment of the present invention.

FIG. 2 sets forth the nucleotide sequence of another portion of the FRS-LOX gene which is inserted into a plant cell genome according to another preferred embodiment of the present invention.

FIG. 3 sets forth the nucleotide sequence of another portion of the FRS-LOX gene which is inserted into a plant cell genome according to another preferred embodiment of the present invention.

FIG. 4 sets forth the nucleotide sequence of the coding region of a tomato FRS-LOX gene cloned and characterized for use in accordance with the present invention.

DESCRIPTION OF THE PREFERRED EMBODIMENTS

Figure 5:
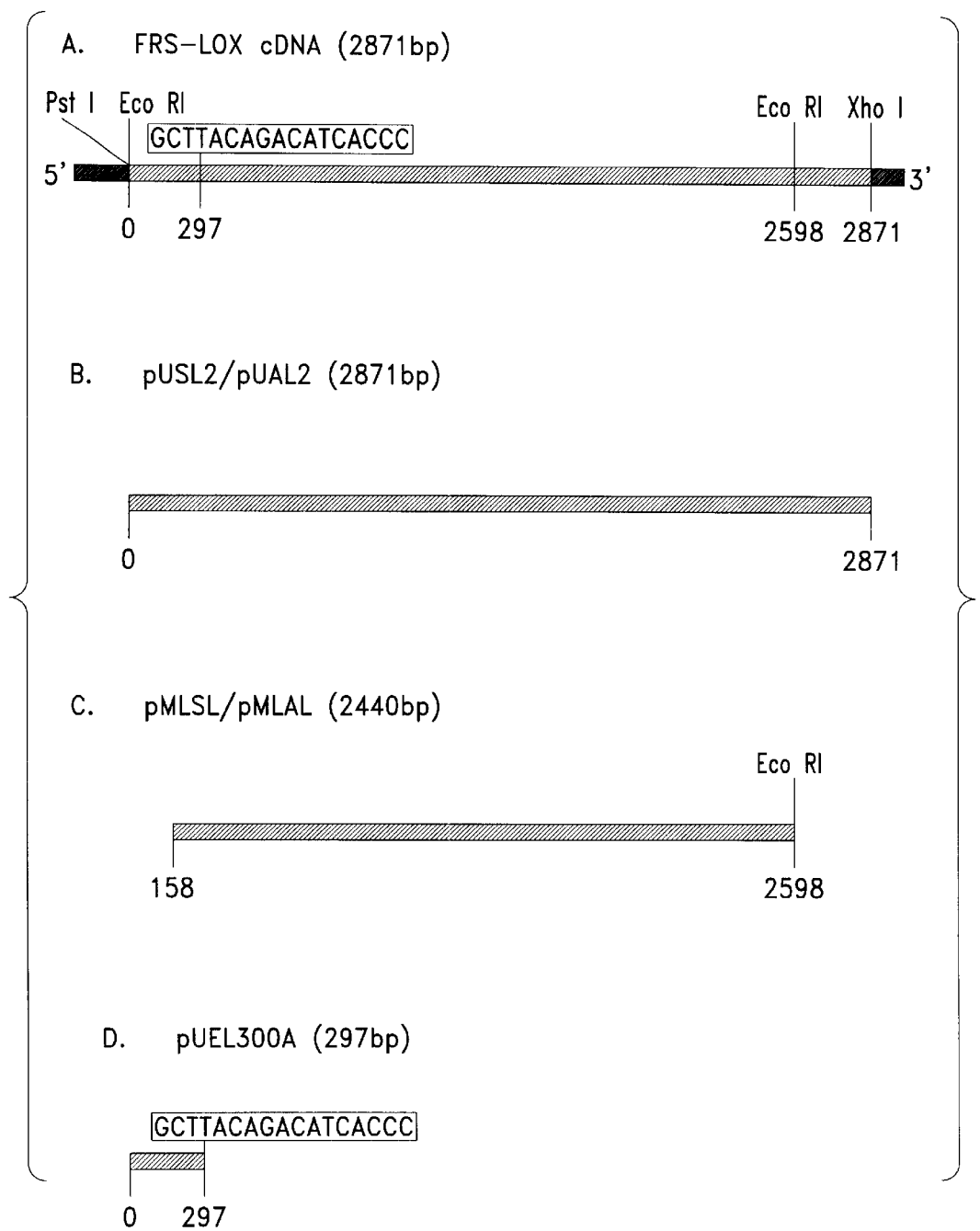
FIG. 5 shows various regions of the tomato FRS-LOX gene used for making vectors according to the present invention.

For the purposes of promoting an understanding of the principles of the invention, references will now be made to certain embodiments and specific language will be used to describe the same. It will nevertheless be understood that no limitation of the scope of the invention is thereby intended. Any alterations and modifications in the invention, and such further applications of the principles of the invention therein being contemplated as would normally occur to one skilled in the art to which the invention relates.

In accordance with the present invention, there are provided transgenic plants and fruits and methods and materials for making them. It has been discovered that the expression of the fruit ripening specific lipoxygenase ("FRS-LOX") gene, and correspondingly, the level of FRS-LOX enzyme activity, are implicated in causing fruit weakening and membrane deterioration in post-maturation fruits. It has also been discovered that these processes can be suppressed in plants by the introduction of a foreign nucleotide sequence having substantial similarity to all or a portion of the coding sequence of the FRS-LOX gene (e.g., as set forth in FIG. 4, SEQ ID NO:4) in either the sense or the antisense orientation. The invention thus provides recombinant DNA with which to achieve such suppression, methods for transforming plants to achieve such suppression, and the resultant transgenic plant cells, transgenic plants and transgenic fruits thereof. The term "substantial similarity," as used herein, is intended to mean sufficiently similar to cause improved fruit quality by inhibiting lipoxygenase production in a fruit when inserted in sense or antisense orientation. For example, it is contemplated that nucleotide sequences useful in the invention will hybridize, under stringent hybridization conditions, to the coding sequence of the FRS-LOX gene (e.g., the nucleotide sequence of SEQ ID NO:4; FIG. 4).

The Examples given below clearly show that the methods of the invention, using the expression of a nucleotide sequence comprising a portion of the FRS-LOX cDNA, results in substantial inhibition of FRS-LOX. Tomato fruit and their seeds, for example, and progeny of these plants will find use in the production of new tomato varieties containing reduced FRS-LOX. These plants are useful in the production of tomatoes of improved quality, which have a longer storage life, better transportablility, better field holding (i.e, fruit lasts longer in good condition on the plant prior to harvest) or be easier to process, and may produce improved products such as whole peeled tomatoes, puree, ketchup or sauces. It will be understood that an FRS-LOX gene appears not only in tomatoes, but also in a wide variety of other plants and that the invention can be used not only for the inhibition of tomato FRS-LOX, but also for the inhibition of FRS-LOX and similar enzymes in various other fruit-bearing plant species. In these other species, of course, the inserted foreign nucleotide sequence must have substantial similarity to all or a portion of the FRS-LOX gene associated with that species.

The preferred aspects of the present invention are carried out using the FRS-LOX gene. The cDNA clone for a tomato FRS-LOX gene (shown in FIG. 4; SEQ ID NO:4) has 2871 nucleotide base pairs and an open reading frame encoding a protein of 859 amino acids with calculated molecular mass of 97 kD and pI of 5.5. Comparison of its sequence reveals 73 and 82 percent similarity at nucleic acid and amino acid levels, respectively, to a LOX cloned from wounded potato tubers which show 5-LOX activity on arachidonic acid (Mulliez et al., Biochem. Biophys. Acta 916,13, 1987; Casey, Plant Physiology 107:265, 1995).

In accordance with the present invention, a nucleotide sequence having substantial similarity to all or a portion of the coding sequence of the FRS-LOX gene (SEQ ID NO:4) is incorporated in a recombinant DNA molecule under the control of a promoter. In this regard, a recombinant DNA molecule is one which has either been naturally or artificially produced from parts derived from heterologous sources, which parts may be naturally occurring or chemically synthesized molecules, and wherein those parts have been joined by ligation or other means known in the art. The introduced FRS-LOX coding sequence is under control of the promoter and thus will be generally downstream from the promoter. Stated alternatively, the promoter sequence will be generally upstream (i.e., at the 5' end) of the coding sequence.

A constitutive promoter was used in the methods described in the Examples below. However, targeting of the gene product can be obtained using a constitutive (e.g. Cauliflower Mosaic Virus 35S promoter), inducible (e.g. Tomato E8 ethylene inducible promoter) or developmentally regulated (e.g. Tomato polygalacturonase promoter) promoter to construct the vectors.

With respect to the function of the promoter, it is well known that there may or may not be other regulatory elements (e.g., enhancer sequences) which cooperate with the promoter and a transcriptional start codon to achieve transcription of the introduced (i.e., foreign) sequence. The phrase "under control of" contemplates the presence of such other elements as are necessary to achieve transcription of the introduced sequence. Such transcription can be assessed, for example, by the detection of the mRNA products of the same. Also, the recombinant DNA will preferably include a termination sequence downstream from the introduced sequence.

The introduced sequence according to the instant invention is preferably a nucleotide sequence having substantial similarity to all or a portion of the nucleotide sequence that encodes the FRS-LOX enzyme (see for example, SEQ ID NO:4). As used herein, the term "portion" is intended to refer to a nucleotide sequence having a sufficient number of nucleotides to cause improved fruit quality by inhibiting lipoxygenase production in a fruit when inserted in sense or antisense orientation. In this regard, coding sequences of about 90 base pairs have been shown to possess inhibitory properties in sense interactions. (See Vaueheret H. (1993) Identification of a General Silencer for 19S and 35S Promoter in a Transgenic Tobacco Plant: 90 bp of homology in the promoter sequence are sufficient for transactivation. C.R. Acad. Sci. III 316:1471–1483.)

According to the present invention, the introduced sequence can have either a sense or an antisense orientation, and can contain nucleotide sequences from any suitable source, including both natural and synthetic sources. In a preferred embodiment, the introduced sequence is one of those of FIGS. 1–3 (SEQ ID NOS:1–3) or one having substantial similarity to one of these sequences, and is incorporated in either a sense or an antisense orientation.

One preferred vector according to the present invention, for example the pMLSL construct, comprises the nucleotide sequence shown in FIG. 1 (SEQ ID NO:1) in the sense orientation (See Example 3, below). The DNA insert shown in SEQ ID NO:1 is a 2440 base pair DNA fragment representing nucleotides 158 to 2598 of the fruit FRS-LOX gene shown in FIG. 4 (SEQ ID NO:4). Another preferred vector, for example the pMLAL construct (See Example 3, below), comprises the same DNA fragment inserted into the vector in the antisense orientation (reverse order).

Another nucleotide sequence which is advantageously inserted into a vector according to the present invention is a sequence containing the full-length FRS-LOX cDNA (SEQ ID NO:4) having 2871 base pairs. This nucleotide sequence is shown in FIG. 2 (SEQ ID NO:2). This sequence may also be inserted in either the sense orientation (See, for example, the pUSL2 construct described in Example 4, below) or the antisense orientation (See, for example, the pUAL2 construct construct described in Example 4, below).

A third nucleotide sequence which is inserted into a vector according to a preferred embodiment of the present invention is a sequence containing nucleotides 1 through 297 of the FRS-LOX gene shown in FIG. 4 (SEQ ID NO:4). This sequence is also set forth in FIG. 3 (SEQ ID NO:3). As with the previously-described sequences, this nucleotide sequence may be inserted into a vector in either the sense orientation (see, for example, the pUEL300S construct described in Example 5, below) or the antisense orientation (see, for example, the pUEL300A construct described in Example 5, below). These vectors are all useful for making inventive transgenic plants as described above.

Additionally contemplated by the present invention is a vector having incorporated therein a nucleotide sequence substantially similar to one of the above-described :nutcleotide sequences.

Suitable nucleotide sequences for use as starting materials in the present invention can be isolated from DNA libraries obtained from other species by means of nucleic acid hybridization or PCP, using as hybridization probes or primers for FRS-LOX, nucleotide sequences that have been published for FRS-LOX genes. Alternatively, antibodies to the FRS-LOX protein can be used to screen a plant cDNA library for clones that express the FRS-LOX protein. The cDNA thus identified as FRS-LOX-protein-encoding can then be used to isolate a genomic clone containing a similar nucleotide sequence or a portion thereof. For an illustrative list of clones obtained in this way, see Table 1 in Example I below.

In accordance with the present invention, the FRS-LOX insertion sequence can be, but is not necessarily, a mutant form. Mutations may include, for example, insertions, deletions, and/or substitutions of one or more nucleotides. Such a mutation in accordance with the invention will provide a coding sequence which, when inserted into a plant in the sense or antisense orientation under the control of a promoter that is expressed in the plant, achieves the suppression of the expression of a natural FRS-LOX gene and the FRS-LOX activity of the transgenic plant.

Recombinant DNA in accordance with the invention can be incorporated into vectors and introduced into the genome of plants using conventional techniques. In this regard, the term "genome" as used herein is intended to refer to DNA which is present in the plant and which is heritable by progeny during propagation of the plant. For example, the invention is illustrated in the Examples below utilizing *Agrobacterium tumefaciens*-mediated transformation, although other techniques can also be used and are within the purview of the ordinarily skilled artisan. The technique used for a given plant species or specific type of plant tissue will depend upon the known successful techniques. Additional means for introducing recombinant DNA into plant tissue include but are not limited to electroporation, microprojectiles, microinjection, as well as other T-DNA mediated transfer from *Agrobacterium tumefaciens*.

Once the recombinant DNA is introduced into the plant tissue, successful transformants can be screened using standard techniques such as the use of marker genes, e.g., genes encoding resistance to antibiotics. Additionally, the level of expression of the natural FRS-LOX gene of transgenic plants may be measured at the transcriptional level or as protein synthesized.

Transgenic plants in accordance with the present invention can also be identified by detection of a significant increase in the firmness of the fruit of the transgenic plant as compared to its wild-type counterparts. The level of firmness of a whole fruit can be determined,for example, by using conventional testing equipment such as a McCormick Fruit Tech (Yakima, Wash.) firmness pressure tester. This tester has a plunger tip and measures the penetration force necessary for the plunger tip to enter the fruit epidermis. In performing these tests, about a 1 cm square section of the waxy epidermis from each fruit was removed where the measurement was to be taken. A minimum of six fruits were analyzed and the mean and standard error were calculated. The results of various firmness tests are given in Table 3 below.

Fruits produced by transgenic plants made according to the present invention are superior to other fruits due to the advantageously modified ripening characteristics including improved quality and texture and greater firmness. These characteristics are believed to result from reduced activity of degradative pathways in the fruit (e.g., membrane deterioration); however, the present invention is not intended to be limited by this theory. These characteristics are economically important, for example, because they impart to the fruit improved shelf life, better packaging and storage characteristics and improved processing characteristics. The present invention provides fruits which are much more easily handled than other fruits, and which are much less likely to be bruised or smashed in the normal course of harvesting, handling, transportation and delivery to a consumer.

According to the present invention, a partial inhibition of lipoxygenase production is adequate for improving fruit quality. Varying levels of inhibition can be obtained by either selecting other transformants, using different fragments of the nucleotide sequence of the FRS-LOX gene (e.g.,SEQ ID NO:4) or using a different promoter, as will be apparent by those skilled in the art. In this regard, preferred transgenics of the invention exhibit at least about a 50% reduction in the level of natural FRS-LOX gene expression or FRS-LOX activity, and in more preferred transgenic plants, reduction is 60% or more. Most preferably, transgenic plants of the invention exhibit at least about 70% reduction of these processes.

Transgenic plants in accordance with the invention can be cultured and reproduced under standard conditions and using standard techniques. Likewise, transgenic fruits obtained from transgenic plants can be conventionally used and processed.

The invention will be further described with reference to the following specific Examples. However, it will be understood that the Examples are offered to further illustrate the present invention, but are not to be construed as limiting the scope thereof.

EXAMPLE ONE

Molecular Cloning of FRS-LOX CDNA

A 90 kd protein that accumulates in the red-ripe fruit of a tomato plant, purified by ammonium sulfate precipitations, ion-exchange chromatography and SDS-PAGE was used to produce polyclonal antibodies in a rabbit. These antibodies were used to immunoscreen more than 150,000 recombinant clones from an expression cDNA library made from poly A+RNA from red-ripe tomato pericarp in the UNI-ZAP XR vector. Among the 24 cDNA clones obtained, 17 clones were similar and had inserts which showed 60–65% homology with the LOX gene family (Gen Bank and EMBL sequence libraries). One of the cDNAs obtained was used to rescreen the cDNA library to obtain a full-length FRS-LOX gene (Kausch and Handa, Plant Physiology 107:669, 1995). FIG. 4 shows the nucleic acid sequence of this gene. Table 1 shows percent similarities of this FRS-LOX gene to LOX clones from other plant species.

TABLE 1

Comparison of the fruit ripening specific lipoxygenase gene sequences at DNA and amino acid levels with other plant Lipoxygenases.

| Lox Gene | Percent Similarity | |
|---|---|---|
| Accession # | Nucleic Acid | Amino Acid |
| Leu09025 | 99.5 | 99.1 |
| Leu09026 | 72.7 | 81.7 |
| Stloxl | 73.2 | 81.6 |
| Athlipoxy | 64.6 | 75.7 |
| Athatlo | 51.6 | 61.4 |
| Pvlipoxy | 64.8 | 74.9 |

TABLE 1-continued

Comparison of the fruit ripening specific
lipoxygenase gene sequences at DNA and amino acid levels
with other plant Lipoxygenases.

| Lox Gene | Percent Similarity | |
|---|---|---|
| Accession # | Nucleic Acid | Amino Acid |
| Soylox | 61.4 | 69.7 |
| Soyloxb | 62.8 | 73.3 |
| Soyloxc | 62.7 | 67.6 |
| Pslipox | 61.4 | 71.9 |
| Gmu04526 | 62.0 | 73.0 |
| Gmu04785 | 54.1 | 71.2 |
| Pslipocy | 61.7 | 73.7 |
| Oslma | 54.1 | 71.2 |
| Ric120p | 48.2 | 61.2 |

EXAMPLE TWO

Construction of Vectors

Several sense and antisense vectors containing different regions of the cloned FRS-LOX (FIG. 4) were made to create transgenic tomato plants. Table 2 summarizes the vectors made and specific procedures used to prepare them are described in Examples 3–6.

TABLE 2

Summary of Sense and Antisense LOX Vectors.

| Name of Sense Vector | Name of Antisense Vector | Insert Size |
|---|---|---|
| pMLSL | pMLAL | 2440 bp |
| pUSL2 | pUAL2 | 2871 bp |
| pUEL300S | pUEL | 300A 297 bp |

EXAMPLE THREE

Construction of pMLSL/pMLAL

1. A 1.7 kb Eco RI and Cla I DNA fragment containing the Cauliflower Mosaic Virus (CaMV 35S) promoter and the small subunit of the Ribulose 1,2-Bisphosphate Carboxylase/Oxygenase (rbcS) 3' terminator with intervening multi-cloning sites was isolated from pKYLX7 (Schardl et al., Gene 61:1, 1987) and cloned into pTZ18U to generate vector pTZ35rbcS.

2. A 2440 bp DNA fragment representing nucleotides 158 to 2598 of the fruit FRS-LOX (FIG. 1, SEQ ID NO:1) was isolated form a partial LOX clone 8-27-1 and ligated into the multi-cloning sites present between the CaMV 35S promoter and rbcS 3' terminator sequences in pTZ35rbcS in both orientations. The clone with the LOX cDNA in the sense orientation relative to the CaMV 35S promoter was named pTZSL, while the clone with the LOX cDNA in the antisense orientation relative to the CaMV 35S promoter designation as pTZAL. Restriction mapping and Southern blotting with CaMV 35S, LOX and rbcS 3' probes and DNA sequencing were used to establish structure of pTZSL and pTZAL.

3. The 4.1 kb DNA fragments containing the CaMV 35S promoter, 2440 bp LOX DNA fragment in sense or antisense orientation and rbcS 3' terminator were obtained from pTZSL or pTZAL, respectively. These fragments were cloned between the Eco RI and Sma I sites in PMLJ1 (an Agrobacterium based transformation vector) both in sense and antisense configuration to obtain PMLSL and pMLAL, respectively. Restriction mapping and Southern blotting with CaMV 35S, LOX and rbcS 3' probes and DNA sequencing were used to establish structures of pMLSL and pMLAL.

EXAMPLE FOUR

Construction of pUSL2/pUAL2

1. A 0.6 k-b DNA fragment (0.6 kb) containing the rbsS terminator was isolated from pTZ35rbcS and cloned at Xba I site of pGEM11Z to create pG11rbcX.

2. The CaMV35S promoter (1.1 kb) was isolated from pTZ35rbcS after digestion with Sac I and Hind III, ligated with Hind III-Eco RI linkers, and forced cloned between Sac I and Eco RI sites of pGllrbcX to create pG35rbcX.

3. The Sac I and Hind III DNA fragment containing CaMV 35S promoter and rbcS terminator isolated from pG35rbcX was blunt ended (using T4 polymerase) and ligated to the blunt ended Apa I and Sal I digested pMLJI to create pML35rbc. This vector (8.45 kb) has been designated as pPUH11.

4. A DNA fragment containing the full-length FRS-LOX CDNA (nucleotide 1 to 2871, See FIG. 2, SEQ ID NO:2) was isolated from clone 10-1#4-1 after digestion with Pst I, and Xho I and blunt-ended with T4 DNA Polymerase. This DNA fragment was cloned in both orientations in the blunt-ended pPUH11 at Xho I site to create pUSL2 (sense) and pUAL2 (antisense) vectors, respectively. Restriction mapping and Southern blotting with CaMV 35S, LOX and rbcS 3' probes and DNA sequencing were used to establish structure of pUSL2 and pUAL2.

EXAMPLE FIVE

Construction of pUEL300s/pUEL300A

1. A DNA fragment containing nucleotides 1 to 297 of FRS-LOX (FIG. 3, SEQ ID NO:3) was obtained after polymerase chain reaction using a LOX-specific primer (a 17-mer oliqnucleotide with the sequence 5' GGGTGAT-GTCTGTAAGC3' corresponding to the nucleotides 297–281) and the T3 Primer (a 17-mer primer specific for the T3 promoter located 90 bp upstream of the FRS-LOX cDNA sequence in pBluescript). This DNA fragment (0.387 kb) was cloned into Eco RV T-tailed pBluescript KS to yield pKSRS17.

2. The LOX specific DNA fragment was obtained from pKSRS17 after Eco RI digestion and cloned in both orientations into an Eco RI digested pPUH11 using T4 DNA ligase to create pUEL300S (sense) and pUEL300A (antisense) chimeric genes, respectively. Restriction mapping and Southern blotting with CaMV 35S, LOX and rbcS 3' probes, and DNA sequencing were used to establish structure of pUEL300S and pUEL300A.

EXAMPLE SIX

Transfer of Vectors to Agrobacterium

The vectors pUSL2, pUAL2, pMLSL, pMLAL, pUEL300S and pUEL300A were mobilized into *Agrobacterium tumefaciens strain pGV*3850 using standard triparental mating techniques with a helper plasmid pGJ23. Transformers were selected using appropriate antibiotics. Total DNA was isolated from selected strains, digested with several endonucleases, separated on agarose gels by electrophoresis, blotted to membrane and hybridized to various probes to confirm the presence of all parts of the respective chimeric gene in Agrobacterium.

EXAMPLE SEVEN

Creation of Transgenic Plants

Cotyledons from eight day old tomato plants were cut and placed on tobacco cell feeder layers for 24 hours before infecting with an Agrobacterium strain (as prepared according to Example 6) harboring plasmid containing a chimeric gene. After a 30 minute infection period, the cotyledons were placed back on the tobacco cell feeder layers and incubated for an additional 48 hours before transferring onto a tomato regeneration medium containing kanamycin and cefotaxime. Every two weeks the explants were subcultured into new regeneration media. Regenerated shoots were rooted using a tomato rooting medium. The rooted plants were removed from tissue culture and placed in a growth chamber in soil for 2 weeks. The plants were then moved to the greenhouse. The presence of the inserted DNA in transgenic plants was confirmed using DNA gel blotting of genomic DNA obtained from transformed (regenerated) tomato plants.

EXAMPLE EIGHT

Level of FRS-LOX mRNA and Protein in Plants Transformed with pMLSL

The levels of FRS-LOX mRNA and protein in ripening fruits from the primary transgenic tomato plants expressing pMLSL analyzed were about 50% of that wild type parental fruits. FRS-LOX mRNA and protein levels were determined using RNA gel blotting and immuno blotting, respectively. Since seeds from these primary transgenic plants segregated in a normal Mendelian manner they are believed to be herterozygous for the introduced pMLSL construct.

EXAMPLE NINE

Effect of Reduced FRS-LOX on Ripening-Associated Fruit Firmness

Figure 6:
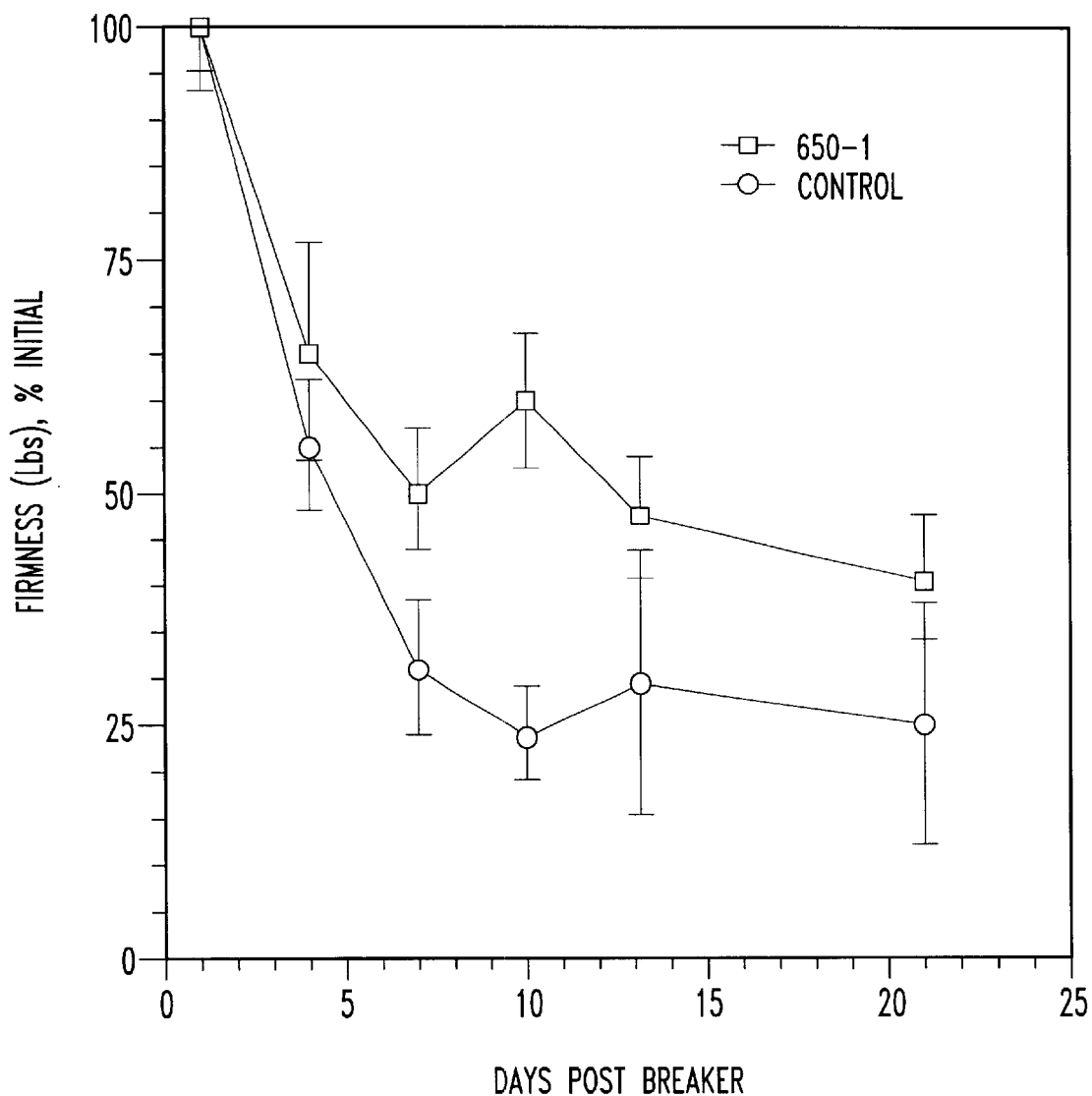
FIG. 6 is a plot of fruit firmness vs. the number of days after breaker for a transgenic tomato of the present invention (650-1) and an Ohio control tomato. "Breaker," as used herein, is intended to denote the time at which a tomato begins to change color from green to orange.

The level of firmness of whole transgenic fruits transformed with the nucleotide sequence of SEQ ID NO:1 in sense orientation were determined by using a McCormick Fruit Tech (Yakima, Wash.) firmness pressure tester. This tester has a plunger tip and measures the penetration force necessary for the plunger tip to enter the fruit epidermis. In performing these tests, about a 1 cm square section of the waxy epidermis from each fruit was removed where the measurement was to be taken. A minimum of six fruits were analyzed and the mean and standard error were calculated. FIG. 6 shows the comparison of ripening-associated fruit firmness over time post breaker in PMSL-650-1 fruits (transgenic tomato transformed with the PMLSL vector) and wild type parental plants. Table 3 shows the firmness of fruits from segregating progeny of PMSL-650-1 with zero, one and two copies of the inserted pMLSL gene. These data clearly demonstrate that reduction of the FRS-LOX inhibits ripening-associated fruit softening.

TABLE 3

Firmness of Fruits from Transgenic Tomato Plant
Containing 0, 1 and 2 copies of inserted pMLSL Gene.

| Days After Breaker | Fruits Firmness, lbs. Copies of Inserted Gene | | |
| --- | --- | --- | --- |
| Stage | 0 | 1 | 2 |
| 7 | 8.85+/−0.96 | 9.51+/−0.67 | 15.51+/−1.94 |
| 10 | 6.29+/−0.49 | 7.43+/−0.42 | 11.46+/−2.93 |

While the invention has been described in detail in the foregoing description, the same is considered as illustrative and not restrictive in character, it being understood that only the preferred embodiments have been shown and described and that all changes and modifications that come within the spirit of the invention are desired to be protected.

---

What is claimed is:

1. A DNA construct selected from the group consisting of pMLSL, pMLAL, pUSL2, pUAL2, pUEL300S and pUEL300A.

2. An isolated polynucleotide having a sequence selected from the group consisting of the sequence of SEQ ID NO:1, the sequence of SEQ ID NO:2, the sequence of SEQ ID NO:3, and the sequence of SEQ ID NO:4.

3. A DNA construct causing a decrease in production of fruit ripening specific lipoxygenase in a plant cell transformed with the construct, the construct comprising an isolated polynucleotide having a sequence selected from the group consisting of the sequence of SEQ ID NO: 1, the sequence of SEQ ID NO:2, the sequence of SEQ ID NO:3, and the sequence of SEQ ID NO:4, wherein the polynucleotide is operably linked to at least one regulatory sequence in either sense or antisense orientation with respect to the regulatory sequence.

4. The DNA construct according to claim 3, wherein the polynucleotide comprises the sequence set forth in SEQ ID NO:1.

5. The DNA construct according to claim 3, wherein the polynucleotide comprises the sequence set forth in SEQ ID NO:2.

6. The DNA construct according to claim 3, wherein the polynucleotide comprises the sequence set forth in SEQ ID NO:3.

7. The DNA construct according to claim 3, wherein the polynucleotide comprises the sequence set forth in SEQ ID NO:4.

8. A transformed plant featuring a decreased production of fruit ripening specific lipoxygenase relative to an untransformed plant, comprising a host plant having incorporated therein a DNA construct causing a decrease in production of fruit ripening specific lipoxygenase, the construct comprising an isolated polynucleotide having a sequence selected from the group consisting of the sequence of SEQ ID NO:1, the sequence of SEQ ID NO:2, the sequence of SEQ ID NO:3, and the sequence of SEQ ID NO:4, wherein the polynucleotide is operably linked to at least one regulatory sequence in either sense or antisense orientation with respect to the regulatory sequence.

9. The transformed plant of claim 8 wherein the host plant is a tomato plant.

10. A method of altering the production of fruit ripening specific lipoxygenase in a plant, comprising stably incorporating into the genome of the plant a DNA construct causing a decrease in production of fruit ripening specific lipoxygenase in a plant cell transformed with the construct, the construct comprising a polynucleotide operably linked to at least one regulatory sequence in either sense or antisense orientation with respect to the regulatory sequence;

wherein the polynucleotide has a sequence selected from the group consisting of the sequence of SEQ ID NO:1, the sequence of SEQ ID NO:2, the sequence of SEQ ID NO:3, and the sequence of SEQ ID NO:4; and wherein said incorporating is achieved by transformation means whereby the incorporated construct causes a decrease in production of fruit ripening specific lipoxygenase in a plant cell containing the polynucleotide as compared to that of an untransformed plant.

11. The method according to claim 10, wherein the polynucleotide comprises the sequence set forth in SEQ ID NO:1.

12. The method according to claim 10, wherein the polynucleotide comprises the sequence set forth in SEQ ID NO:2.

13. The method according to claim 10, wherein the polynucleotide comprises the sequence set forth in SEQ ID NO:3.

14. The method according to claim 10, wherein the polynucleotide comprises the sequence set forth in SEQ ID NO:4.

* * * * *

UNITED STATES PATENT AND TRADEMARK OFFICE
CERTIFICATE OF CORRECTION

PATENT NO.    : 6,355,862 B1
DATED         : March 12, 2002
INVENTOR(S)   : Handa et al.

It is certified that error appears in the above-identified patent and that said Letters Patent is hereby corrected as shown below:

Column 1,
Line 9, before the heading "BACKGROUND OF THE INVENTION" insert the following paragraph:

-- ACKNOWLEDGMENT OF FEDERAL RESEARCH SUPPORT

This invention was made with Government support under USDA Grant No. 90-34190-5207. The Government has certain rights in this invention. --

Signed and Sealed this

Seventeenth Day of December, 2002

JAMES E. ROGAN
*Director of the United States Patent and Trademark Office*

SEQUENCE LISTING

<160> NUMBER OF SEQ ID NOS: 4

<210> SEQ ID NO 1
<211> LENGTH: 2441
<212> TYPE: DNA
<213> ORGANISM: Lycopersicon esculentum

<400> SEQUENCE: 1

```
ttcagttgtt gatggcattt ctgatttact tggccaaaaa gtctctatcc          50
aattgataag tggttctgtt aattatgatg gtttggaagg gaaactgagc         100
aatccagcat acttagagag ttggcttaca gacatcaccc caataacagc         150
aggggaatca acttttagtg ttacatttga ctgggatcgt gacgagtttg         200
gagttccagg agcattcatc atcaagaatc ttcatcttaa tgagttcttt         250
ctcaagtcac tcacactcga agatgttcct aattatggaa aaatccattt         300
tgtatgcaat tcttgggttt atcctgcttt tagatacaag tctgaccgca         350
ttttctttgc caatcaggct tatctcccaa gtgaaacacc acaaccattg         400
cgaaaataca gagaaaatga actggtagct ttgcgaggag atggaactgg         450
```

-continued

| | |
|---|---|
| aaagcttgaa gaatgggaca gggtttatga ttatgcttgc tacaatgact | 500 |
| tgggtgaacc agataagggg gaagagtatg ctaggcctat ccttggaggg | 550 |
| tcctctgagt acccgtatcc tcgtagaggc aggacaggcc gcgaaccaac | 600 |
| caaagcagat cctaattgcg agagcaggaa cccattgcct atgagcttag | 650 |
| acatatatgt cccaagggac gagcgatttg gtcatgtgaa gaagtcagac | 700 |
| tttttgacgt cgtccttaaa atcctctttg caaacgcttc tccctgcgtt | 750 |
| taaggctttg tgcgataaca cgcctaatga gttcaatagc tttgcggatg | 800 |
| tacttaatct ctatgaagga ggaatcaagt tgcctgaagg cccttggttg | 850 |
| aaagccatta ctgataacat ttcctcagag atactaaaag acatccttca | 900 |
| aacggatggt caaggcctac ttaagtaccc aactcctcag gttattcaag | 950 |
| gcgataaaac tgcatggagg acggatgaag aatttgggag agaaatgttg | 1000 |
| gcaggatcca atcctgtctt aatcagtaga ctccaagaat ttcctccgaa | 1050 |
| gagcaagttg gatccaacca tatatggaaa ccaaaacagt acaattacca | 1100 |
| cagaacatgt acaggataag ttgaatggat taacagtgaa tgaggcaatc | 1150 |
| aagagtaaca ggttattcat attgaaccac catgacatcg tgatgccact | 1200 |
| attgaggaaa attaacatgt cagcaaacac aaaagcctat gcctcaagaa | 1250 |
| ctctgctctt cctacaagat gatagaactt tgaagccact agcaattgaa | 1300 |
| ctaagcttgc cacatccaga cggagatcaa tttggtactg ttagtaaagt | 1350 |
| atatacacca gctgaccaag gtgttgaagg ttctatctgg cagtttgcca | 1400 |
| aagcctatgt agcagtgaat gacatgggca ttcatcagct cattagccac | 1450 |
| tggttgaata cacacgcggt gatcgaacca tttgtgattg caacaaatag | 1500 |
| gcatctaagt gtgcttcatc ccattcataa acttcttcat cctcatttcc | 1550 |
| gtaacacgat gaacataaat gctttagcaa gagagacctt gacctatgat | 1600 |
| ggtggttttg agacgtctct ttttcctgcc aaatattcca tggaaatgtc | 1650 |
| agcagcagct tacaaagatt gggttttccc tgaacaagca cttcctgctg | 1700 |
| atctcctcaa aagaggagtg gctgttgagg acttgagctc cccacatggc | 1750 |
| attcgtttac tgattctgga ctatccatat gctgttgatg gcttggaaat | 1800 |
| ttgggcagca atcaaaagtt gggtaacaga atattgcaag ttctattaca | 1850 |
| aatctgacga gacagtagag aaagacactg aactccaagc ttggtggaag | 1900 |
| gagctccgcg aagaaggaca tggcgacaag aaagatgagg cttggtggcc | 1950 |
| taaactgcaa actcgacaag agctcagaga ttgttgcacc atcattatat | 2000 |
| ggatagcttc agcacttcat gcagcactcc attttggctt atactcttac | 2050 |
| gctggttatc tccctaatcg ccctacttta agctgtaatt tgatgccaga | 2100 |
| gccaggaagt gttgagtatg aagagctcaa gacaaatcca gacaaggtat | 2150 |
| tcctaaaaac atttgttcct cagttgcaat cactgcttga aatttccatc | 2200 |
| tttgaggtct cgtcaaggca tgcttcagat gaggtttact tgggacaaag | 2250 |
| ggactcaatt gaatggacaa aggataaaga accacttgta gcttttgaga | 2300 |
| ggtttggaaa gatgctaagt gatatcgaga atcgaattat gataatgaat | 2350 |
| agtcataaga gttggaagaa caggtcaggg cctgttaacg ttccatatac | 2400 |

| | |
|---|---:|
| gttgctcttt cccacaagtg aagagggact cacaggcaaa g | 2441 |

<210> SEQ ID NO 2
<211> LENGTH: 2871
<212> TYPE: DNA
<213> ORGANISM: Lycopersicon esculentum

<400> SEQUENCE: 2

| | |
|---|---:|
| tttctctaat taaaaaaaaa atatttctgt ttaaatagtt aatcatgtct | 50 |
| ttgggtggaa ttgtggatgc catccttgga aaagatgata ggccaaaagt | 100 |
| gaaaggaaga gtgattttga tgaaaaaaaa tgttctagac ttcattaata | 150 |
| taggtgcttc agttgttgat ggcatttctg atttacttgg ccaaaaagtc | 200 |
| tctatccaat tgataagtgg ttctgttaat tatgatggtt tggaagggaa | 250 |
| actgagcaat ccagcatact tagagagttg gcttacagac atcaccccaa | 300 |
| taacagcagg ggaatcaact tttagtgtta catttgactg ggatcgtgac | 350 |
| gagtttggag ttccaggagc attcatcatc aagaatcttc atcttaatga | 400 |
| gttctttctc aagtcactca cactcgaaga tgttcctaat tatggaaaaa | 450 |
| tccattttgt atgcaattct tgggtttatc ctgcttttag atacaagtct | 500 |
| gaccgcattt tctttgccaa tcaggcttat ctcccaagtg aaacaccaca | 550 |
| accattgcga aaatacagag aaaatgaact ggtagctttg cgaggagatg | 600 |
| gaactggaaa gcttgaagaa tgggacaggg tttatgatta tgcttgctac | 650 |
| aatgacttgg gtgaaccaga taaggggggaa gagtatgcta ggcctatcct | 700 |
| tggagggtcc tctgagtacc cgtatcctcg tagaggcagg acaggccgcg | 750 |
| aaccaaccaa agcagatcct aattgcgaga gcaggaaccc attgcctatg | 800 |
| agcttagaca tatatgtccc aagggacgag cgatttggtc atgtgaagaa | 850 |
| gtcagacttt ttgacgtcgt ccttaaaatc ctctttgcaa acgcttctcc | 900 |
| ctgcgtttaa ggctttgtgc gataacacgc taatgagtt caatagcttt | 950 |
| gcggatgtac ttaatctcta tgaaggagga atcaagttgc ctgaaggccc | 1000 |
| ttggttgaaa gccattactg ataacatttc ctcagagata ctaaaagaca | 1050 |
| tccttcaaac ggatggtcaa ggcctactta agtacccaac tcctcaggtt | 1100 |
| attcaaggcg ataaaactgc atggaggacg atgaagaat ttgggagaga | 1150 |
| aatgttggca ggatccaatc ctgtcttaat cagtagactc caagaatttc | 1200 |
| ctccgaagag caagttggat ccaaccatat atggaaacca aaacagtaca | 1250 |
| attaccacag aacatgtaca ggataagttg aatggattaa cagtgaatga | 1300 |
| ggcaatcaag agtaacaggt tattcatatt gaaccaccat gacatcgtga | 1350 |
| tgccactatt gaggaaaatt aacatgtcag caaacacaaa agcctatgcc | 1400 |
| tcaagaactc tgctcttcct acaagatgat agaactttga agccactagc | 1450 |
| aattgaacta agcttgccac atccagacgg agatcaattt ggtactgtta | 1500 |
| gtaaagtata taccagct gaccaaggtg ttgaaggttc tatctggcag | 1550 |
| tttgccaaag cctatgtagc agtgaatgac atgggcattc atcagctcat | 1600 |
| tagccactgg ttgaatacac acgcggtgat cgaaccattt gtgattgcaa | 1650 |
| caaataggca tctaagtgtg cttcatccca ttcataaact tcttcatcct | 1700 |
| catttccgta acacgatgaa cataaatgct ttagcaagag agaccttgac | 1750 |

-continued

```
ctatgatggt ggttttgaga cgtctctttt tcctgccaaa tattccatgg         1800
aaatgtcagc agcagcttac aaagattggg ttttccctga caagcactt          1850 cctgctgatc tcctcaaaag aggagtggct gttgaggact tgagctcccc         1900
acatggcatt cgtttactga ttctggacta tccatatgct gttgatggct         1950
tggaaatttg ggcagcaatc aaaagttggg taacagaata ttgcaagttc         2000
tattacaaat ctgacgagac agtagagaaa gacactgaac tccaagcttg         2050
gtggaaggag ctccgcgaag aaggacatgg cgacaagaaa gatgaggctt         2100
ggtggcctaa actgcaaact cgacaagagc tcagagattg ttgcaccatc         2150
attatatgga tagcttcagc acttcatgca gcactccatt ttggcttata         2200
ctcttacgct ggttatctcc ctaatcgccc tactttaagc tgtaatttga         2250
tgccagagcc aggaagtgtt gagtatgaag agctcaagac aaatccagac         2300
aaggtattcc taaaaacatt tgttcctcag ttgcaatcac tgcttgaaat         2350
ttccatcttt gaggtctcgt caaggcatgc ttcagatgag gtttacttgg         2400
gacaaaggga ctcaattgaa tggacaaagg ataagaacc acttgtagct          2450 tttgagaggt ttggaaagat gctaagtgat atcgagaatc gaattatgat         2500
aatgaatagt cataagagtt ggaagaacag gtcagggcct gttaacgttc         2550
catatacgtt gctctttccc acaagtgaag agggactcac aggcaaagga         2600
attcccaaca gtgtgtctat atagaactta ttattcaatc agtttgttgt         2650
gcttgtgtta cttgttattc ccaaccaaat aaactctttg ttccaaataa         2700
agagtattgt attgtattgt cttgtgtgtt gtgttgtatt gtattatatt         2750
gtatagtatt attgatttaa atacaatgtt tgttgcactt gtttcttgtt         2800
attcccaacc aaataaactc tttgttccaa ataaagctgt agttggtttt         2850
aaaaaaaaaa aaaaaaaaaa a                                        2871
```

<210> SEQ ID NO 3
<211> LENGTH: 297
<212> TYPE: DNA
<213> ORGANISM: Lycopersicon esculentum

<400> SEQUENCE: 3

```
ttttcttaat taaaaaaaaa atatttctgt ttaaatagtt aatcatgtct         50
ttgggtggaa ttgtggatgc catccttgga aaagatgata ggccaaaagt         100
gaaaggaaga gtgattttga tgaaaaaaaa tgttctagac ttcattaata         150
taggtgcttc agttgttgat ggcatttctg atttacttgg ccaaaaagtc         200
tctatccaat tgataagtgg ttctgttaat tatgatggtt tggaagggaa         250
actgagcaat ccagcatact tagagagttg gcttacagac atcaccc            297
```

<210> SEQ ID NO 4
<211> LENGTH: 2871
<212> TYPE: DNA
<213> ORGANISM: Lycopersicon esculentum

<400> SEQUENCE: 4

```
ttttcttaat taaaaaaaaa atatttctgt ttaaatagtt aatcatgtct         50
ttgggtggaa ttgtggatgc catccttgga aaagatgata ggccaaaagt         100
```

-continued

| | |
|---|---|
| gaaaggaaga gtgattttga tgaaaaaaaa tgttctagac ttcattaata | 150 |
| taggtgcttc agttgttgat ggcatttctg atttacttgg ccaaaaagtc | 200 |
| tctatccaat tgataagtgg ttctgttaat tatgatggtt tggaagggaa | 250 |
| actgagcaat ccagcatact tagagagttg gcttacagac atcaccccaa | 300 |
| taacagcagg ggaatcaact tttagtgtta catttgactg ggatcgtgac | 350 |
| gagtttggag ttccaggagc attcatcatc aagaatcttc atcttaatga | 400 |
| gttcttctc aagtcactca cactcgaaga tgttcctaat tatggaaaaa | 450 |
| tccatttgt atgcaattct tgggtttatc ctgcttttag atacaagtct | 500 |
| gaccgcattt tctttgccaa tcaggcttat ctcccaagtg aaacaccaca | 550 |
| accattgcga aaatacagag aaaatgaact ggtagctttg cgaggagatg | 600 |
| gaactggaaa gcttgaagaa tgggacaggg tttatgatta tgcttgctac | 650 |
| aatgacttgg gtgaaccaga taaggggggaa gagtatgcta ggcctatcct | 700 |
| tggagggtcc tctgagtacc cgtatcctcg tagaggcagg acaggccgcg | 750 |
| aaccaaccaa agcagatcct aattgcgaga gcaggaaccc attgcctatg | 800 |
| agcttagaca tatatgtccc aagggacgag cgatttggtc atgtgaagaa | 850 |
| gtcagacttt ttgacgtcgt ccttaaaatc ctctttgcaa acgcttctcc | 900 |
| ctgcgtttaa ggctttgtgc gataacacgc ctaatgagtt caatagcttt | 950 |
| gcggatgtac ttaatctcta tgaaggagga atcaagttgc ctgaaggccc | 1000 |
| ttggttgaaa gccattactg ataacatttc ctcagagata ctaaaagaca | 1050 |
| tccttcaaac ggatggtcaa ggcctactta agtacccaac tcctcaggtt | 1100 |
| attcaaggcg ataaaactgc atggaggacg gatgaagaat tgggagaga | 1150 |
| aatgttggca ggatccaatc ctgtcttaat cagtagactc caagaatttc | 1200 |
| ctccgaagag caagttggat ccaaccatat atggaaacca aaacagtaca | 1250 |
| attaccacag aacatgtaca ggataagttg aatggattaa cagtgaatga | 1300 |
| ggcaatcaag agtaacaggt tattcatatt gaaccaccat gacatcgtga | 1350 |
| tgccactatt gaggaaaatt aacatgtcag caaacacaaa agcctatgcc | 1400 |
| tcaagaactc tgctcttcct acaagatgat agaactttga agccactagc | 1450 |
| aattgaacta agcttgccac atccagacgg agatcaattt ggtactgtta | 1500 |
| gtaaagtata taccagct gaccaaggtg ttgaaggttc tatctggcag | 1550 |
| tttgccaaag cctatgtagc agtgaatgac atgggcattc atcagctcat | 1600 |
| tagccactgg ttgaatacac acgcggtgat cgaaccattt gtgattgcaa | 1650 |
| caaataggca tctaagtgtg cttcatccca ttcataaact tcttcatcct | 1700 |
| catttccgta acacgatgaa cataaatgct ttagcaagag agaccttgac | 1750 |
| ctatgatggt ggttttgaga cgtctctttt tcctgccaaa tattccatgg | 1800 |
| aaatgtcagc agcagcttac aaagattggg ttttccctga caagcactt | 1850 |
| cctgctgatc tcctcaaaag aggagtggcc gttgaggact tgagctcccc | 1900 |
| acatggcatt cgtttactga ttctggacta tccatatgct gttgatggct | 1950 |
| tggaaatttg ggcagcaatc aaaagttggg taacagaata ttgcaagttc | 2000 |
| tattacaaat ctgacgagac agtagagaaa gacactgaac tccaagcttg | 2050 |
| gtggaaggag ctccgcgaag aaggacatgg cgacaagaaa gatgaggctt | 2100 |

```
ggtggcctaa actgcaaact cgacaagagc tcagagattg ttgcaccatc      2150
attatatgga tagcttcagc acttcatgca gcactccatt ttggcttata      2200
ctcttacgct ggttatctcc ctaatcgccc tactttaagc tgtaatttga      2250
tgccagagcc aggaagtgtt gagtatgaag agctcaagac aaatccagac      2300
aaggtattcc taaaaacatt tgttcctcag ttgcaatcac tgcttgaaat      2350
ttccatcttt gaggtctcgt caaggcatgc ttcagatgag gtttacttgg      2400
gacaaaggga ctcaattgaa tggacaaagg ataaagaacc acttgtagct      2450
tttgagaggt ttggaaagat gctaagtgat atcgagaatc gaattatgat      2500
aatgaatagt cataagagtt ggaagaacag gtcagggcct gttaacgttc      2550
catatacgtt gctctttccc acaagtgaag agggactcac aggcaaagga      2600
attcccaaca gtgtgtctat atagaactta ttattcaatc agtttgttgt      2650
gcttgtgtta cttgttattc ccaaccaaat aaactctttg ttccaaataa      2700
agagtattgt attgtattgt cttgtgtgtt gtgttgtatt gtattatatt      2750
gtatagtatt attgatttaa atacaatgtt tgttgcactt gtttcttgtt      2800
attcccaacc aaataaactc tttgttccaa ataaagctgt agttggtttt      2850
aaaaaaaaaa aaaaaaaaa a                                     2871
```